US006635034B1

(12) United States Patent
Cosmescu

(10) Patent No.: US 6,635,034 B1
(45) Date of Patent: Oct. 21, 2003

(54) MULTIFUNCTIONAL HANDPIECE FOR USE IN OPEN AND LAPAROSCOPIC LASER SURGERY AND ELECTROSURGERY

(76) Inventor: Ioan Cosmescu, 1449 N. 22nd St., Phoenix, AZ (US) 85022

( * ) Notice: Subject to any disclaimer, the term of this patent is extended or adjusted under 35 U.S.C. 154(b) by 0 days.

(21) Appl. No.: 09/607,685

(22) Filed: Jun. 30, 2000

Related U.S. Application Data

(62) Division of application No. 09/192,887, filed on Nov. 16, 1998, which is a continuation of application No. 08/713,447, filed on Sep. 13, 1996, now Pat. No. 5,836,909.

(51) Int. Cl.⁷ ............................................. A61M 1/00
(52) U.S. Cl. ..................... 604/289; 601/35; 604/119; 606/46
(58) Field of Search ................... 604/289, 21, 33, 604/35, 119, 27; 601/35; 600/108, 158, 131; 606/15, 2, 288

(56) References Cited

U.S. PATENT DOCUMENTS

| 3,527,203 A | 9/1970 | Gravlee |
| 4,149,315 A | 4/1979 | Page, Jr. et al. |
| 4,493,694 A | 1/1985 | Wuchinich |
| 4,744,360 A | 5/1988 | Bath |
| 4,776,840 A | 10/1988 | Freitas et al. |
| 5,195,958 A | 3/1993 | Phillips |
| 5,607,391 A | 3/1997 | Klinger et al. |
| 5,607,420 A | 3/1997 | Schuman |
| 5,658,249 A | 8/1997 | Beland et al. |
| 5,685,877 A | 11/1997 | Pagedas et al. |
| 5,836,909 A | * 11/1998 | Cosmescu ................... 601/35 |

* cited by examiner

Primary Examiner—Kim M. Lewis
(74) Attorney, Agent, or Firm—Snell & Wilmer, L.L.P.

(57) ABSTRACT

A manual and automatic fluid control system and method for use in open and laparoscopic laser surgery and electrosurgery is disclosed. The system includes a manual mode along with several automatic modes which can effectuate both suction and irrigation, either individually or simultaneously. In the various automatic modes, the suction and/or irrigation is automatically activated during activation of a medical apparatus for laser surgery or electrosurgery without requiring separate activation from the surgeon or operating room staff. Several safety features for monitoring the fluid control system are also incorporated within the system such as fluid sensors for detecting the absence of irrigation fluid, pressure sensors and vacuum systems for monitoring fluid pressure, fluid sensors for monitoring fluid volume, and warning signals for detecting empty containers. All of the safety features are designed to automatically deactivate suction and/or irrigation means contained within the fluid control system upon detection of unsafe levels. Finally, specially designed suction/irrigation hand pieces are disclosed for use in connection with the fluid control system.

6 Claims, 7 Drawing Sheets

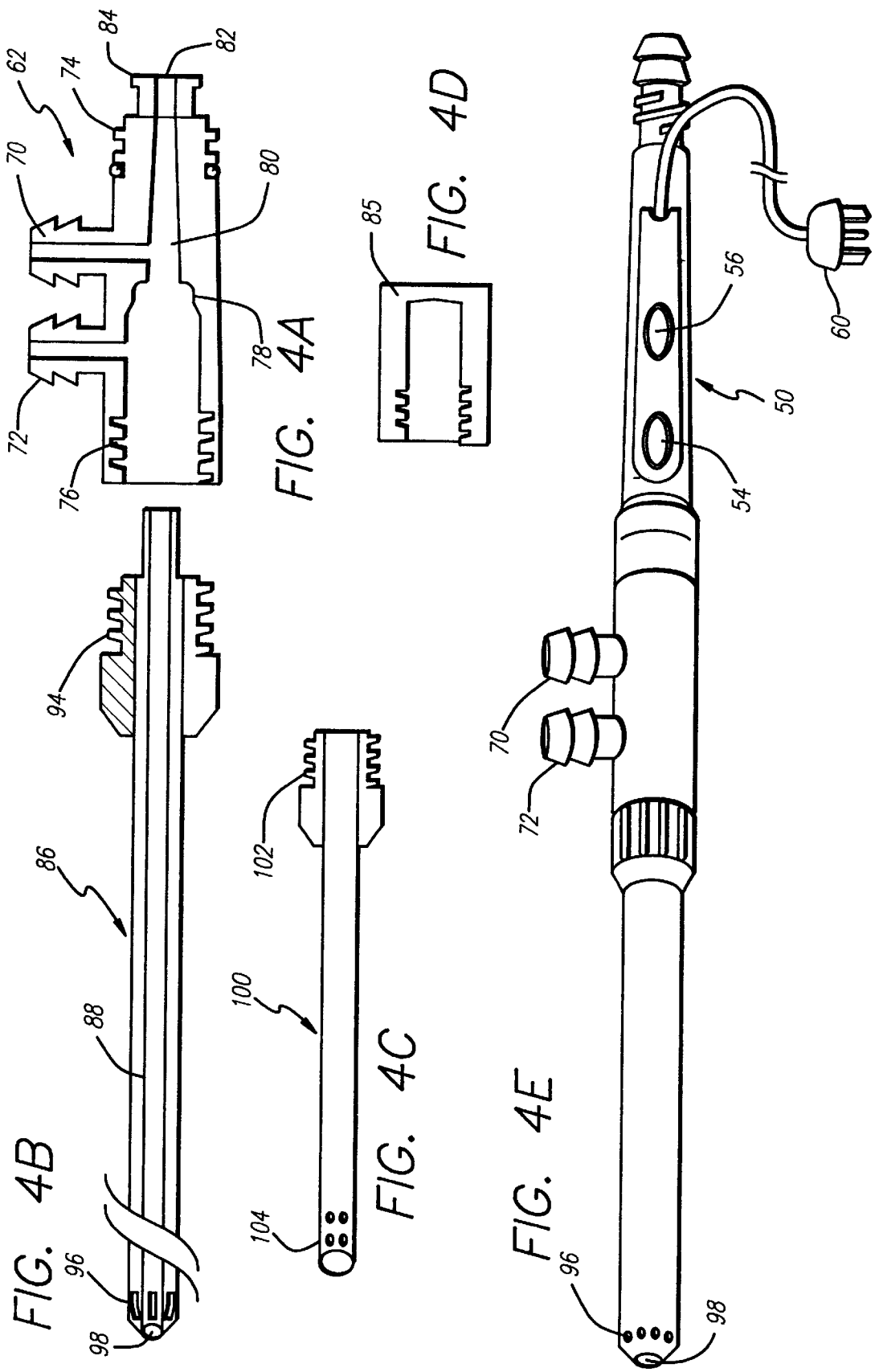

MULTIFUNCTIONAL HANDPIECE FOR USE IN OPEN AND LAPAROSCOPIC LASER SURGERY AND ELECTROSURGERY

RELATED APPLICATIONS

This application is a divisional application of U.S. patent application Ser. No. 09/192,887, filed Nov. 16, 1998 and entitled "AUTOMATIC FLUID CONTROL SYSTEM FOR USE IN OPEN AND LAPAROSCOPIC LASER SURGERY AND ELECTROSURGERY AND METHOD THEREFOR", which is a continuation application of U.S. patent application Ser. No. 08/713,447, filed Sep. 13, 1996 and entitled "AUTOMATIC FLUID CONTROL SYSTEM FOR USE IN OPEN AND LAPAROSCOPIC LASER SURGERY AND ELECTROSURGERY AND METHOD THEREFOR", which application issued as U.S. Pat. No. 5,836,909 on Nov. 17, 1998. This patent application is also related to my earlier patents entitled "AUTOMATIC SMOKE EVACUATOR SYSTEM FOR A SURGICAL LASER APPARATUS AND METHOD THEREFOR" issued Apr. 6, 1993 as U.S. Pat. No. 5,199,944 and "TELESCOPIC SURGICAL DEVICE AND METHOD THEREFOR" issued Dec. 2, 1997 as U.S. Pat. No. 5,693,044. Both issued patents are herein incorporated by reference.

BACKGROUND OF THE INVENTION

1. Field of the Invention

The present invention relates generally to an automatic fluid control system and method and suction/irrigation hand pieces which are designed to be used in conjunction with the automatic fluid control system and method. More particularly, the present invention relates to an automatic fluid control system and method which can effectuate both suction and irrigation, either individually or simultaneously, and which has a re-useable pump that can deliver high pressure and high flow suction and irrigation which are required during open and laparoscopic laser surgery and electrosurgery procedures.

2. Description of the Prior Art

In the past, suction/irrigation units have functioned by applying air pressure on water containers, wherein the water is being used for fluid irrigation, in order to force the water to be pressurized. A trumpet valve was used to release the water under relative pressure for laparoscopic procedures. These devices operated under low pressure due to the risk of exploding the irrigation containers in the event that too much pressure was applied. Consequently, both the water pressure and water flow associated with those devices were low. Further, the trumpet valve associated with these devices is relatively hard to handle because of the strong springs that are necessary to enable the valves to function.

Another suction/irrigation device has been designed to include a disposable electric pump. This design is an improved version of the previously described design but is very expensive in that the pump is disposable. Further, the pump is battery operated and very small, thereby resulting in inadequate flow and pressure to obtain good irrigation during hydro-dissection. A modified version of the trumpet valve is also used, but it is hard to handle and expensive.

None of the previously described suction/irrigation units and trumpet valves are capable of performing irrigation and suction simultaneously. Simultaneous suction and irrigation would reduce the operating time and greatly improve the visibility of the tissue for the operator. In addition, electrosurgery was not possible with the trumpet valve, and a, special device had to be used which further increased the cost per operation.

SUMMARY OF THE INVENTION

It is a principle object of the present invention to provide a fluid control system and method which is capable of effectuating both suction and irrigation, both individually and simultaneously, and which has a reusable pump that can deliver high pressure and high flow for suction/irrigation and hydro-dissection.

It is a further object of the present invention to provide an automatic fluid control system and method that will automatically employ suction and/or irrigation for a desired time period, where suction and/or irrigation are necessary, without requiring separate activation from the surgeon or operating room staff.

It is still a further object of the present invention to provide an automatic fluid control system and method that is safe and easy to use and which is capable of monitoring the water pressure, the vacuum, and the volume of fluid entering into, and being evacuated from, the patient in order to automatically turn the system off when the pressure or the vacuum exceed the desired limits.

It is yet a further object of the present invention to provide an automatic fluid control system and method wherein both suction and irrigation can be operated either separately or simultaneously, and either manually or automatically.

It is still a further object of the present invention to provide a fluid control system and method which can separately perform Cysto Turp by being activated either automatically and/or manually and which measures and monitors the fluid volume and/or fluid flow into, and out of, the patient such that the irrigation pump is automatically deactivated when fluid inflow exceeds fluid outflow. Another safety feature for performing Cysto Turp includes means for monitoring fluid pressure wherein the irrigation pump is automatically deactivated upon reaching a dangerously high fluid pressure level.

It is yet a further object of the present invention to provide a hand piece which can be used in conjunction with the automatic fluid control system and method of the present invention and which will replace the trumpet valve of previous devices. The hand piece of the present invention combined with the automatic fluid control system of the present invention can be used to perform laparoscopic and open procedures while employing suction and irrigation either separately or simultaneously. The combined hand piece and automatic fluid control system and method of the present invention can also be used to perform open or laparoscopic electrosurgery and smoke evacuation. Further, the hand piece may comprise a retractable electrode which enables the electrode to be retracted within the channel for suction and/or irrigation so that the suction and/or irrigation port will be clear of obstruction. This can be evidenced by attaching the automatic fluid control system of the present invention to the telescopic surgical device described in my previous patent application entitled "A Telescopic Surgical Device and Method Therefor", Serial No. 08/500,045. This telescopic surgical device includes switches which can be used for turning the suction and irrigation "on" and "off". Combining the telescopic surgical device with the automatic fluid control system of the present invention will result in making the telescopic surgical device a multi functional hand piece thereby enabling it to handle both open and laparoscopic electrosurgery, both open and laparoscopic argon beam coagulation, and suction/irrigation for both open and laparoscopic procedures.

Accordingly, the automatic fluid control system of the present invention is first directed to a manual fluid control system for surgical lasers and electrosurgery apparatus, for both open and laparoscopic procedures, which includes at least one fluid irrigation container, irrigation tubing connected to the fluid irrigation container, a valve connected to the irrigation tubing for accessing the irrigation fluid in the container, means for pumping the irrigation fluid through the tubing to a surgery site within a patient, suction tubing connected to a suctioning container, and means for suctioning fluids through the suction tubing from the surgery site in the patient.

A second embodiment of the fluid control system of the present invention is directed to an automatic fluid control system for surgical lasers and electrosurgery apparatus, for both open and laparoscopic procedures, which includes at least one fluid irrigation container, an irrigation tubing connected to the irrigation container, a valve connected to the irrigation tubing for accessing the irrigation fluid within the container, means for employing a surgical device, means for irrigating the irrigation fluid through the irrigation tubing to a site of the surgical device wherein the irrigation means is connected to the surgical device employment means such that the irrigation means is activated upon deactivation of the surgical device, a suction tubing connected to a suction container, and means for suctioning fluid from a patient through the suction tubing at the site of the surgical device wherein the suctioning means is connected to the irrigation means such that the suctioning means is activated upon deactivation of the irrigation means. Further, a third embodiment of the fluid control system of the present invention is directed to an automatic fluid control system for surgical lasers and electrosurgery apparatus, for both open and laparoscopic procedures, as that previously described with reference to the second embodiment, with the exception that the irrigation means is activated upon deactivation of the surgical device and the suctioning means is activated upon activation of the irrigation means and then deactivated at a short predetermined time following deactivation of the irrigation means. Finally, a fourth embodiment of the fluid control system of the present invention is directed to an automatic fluid control system for surgical lasers and electrosurgery apparatus, for both open and laparoscopic procedures, such as that previously described with reference to the second embodiment, with the exception that the suctioning means is activated upon activation of the surgical device employment means and the irrigation means is activated upon activation of the suctioning means.

All of the previously described embodiments may also include additional safety features including, but not limited to, the following: (1) a fluid sensor for detecting the presence of irrigation fluid within the irrigation tubing and a safety relay for shutting off the irrigation means when irrigation fluid is not present within the irrigation tubing, (2) a pressure sensor connected to the irrigation tubing which is in turn connected to a pressure controller capable of shutting off the irrigation means upon detection of an unsafe fluid pressure level, (3) a container controller connected to the safety relay which is capable of switching irrigation means from an empty container to another full container, (4) an alarm element connected to the container controller which activates a voice or warning signal indicating that the presently used fluid irrigation container is empty, and (5) a vacuum sensor connected to the suction tubing having means for disconnecting the suctioning means and irrigation means upon the detection of an unsafe vacuum pressure. The previously described embodiments may also include a flow meter sensor connected to the irrigation tubing and a suction flow meter sensor connected to the suction tubing wherein signals received from the flow meter sensor and suction flow meter sensor are received and evaluated by a counter which is capable of reporting differences in fluid flow rates and fluid volumes entering and exiting the patient, and which in turn can automatically shut off the irrigation pump upon detecting dangerously high levels.

The objectives, features and advantages of the present invention will become more apparent to those skilled in the art from the following more detailed description of the preferred embodiments of the invention made in conjunction with the accompanying drawings.

BRIEF DESCRIPTION OF THE DRAWINGS

FIG. 4A is a cross sectional view of the suction/irrigation connector of the present invention which is designed to be connected between a suction/irrigation tube shown in FIG. 4B and a hand piece such as that shown in FIG. 3.

FIG 4B shows a cross sectional view of a suction/irrigation tube wherein irrigation and suction can be performed simultaneously.

FIG. 4C is a side elevational view of a suction/irrigation tube which enables only separate suction or irrigation when used in conjunction with the fluid control system of the present invention.

FIG. 4D is a cross-sectional view of a cap which can be placed over the posterior end of the suction/irrigation connector shown in FIG. 4A when the fluid control system is used alone and not in connection with open and laparoscopic electrosurgery.

FIG. 4E is a top elevational view of the resulting hand piece of the present invention which includes the connection of a section/irrigation tube to the suction/irrigation connector which is in turn connected to a hand-piece having switches for employing suction and irrigation.

DESCRIPTION OF THE PREFERRED EMBODIMENTS

Figure 1:
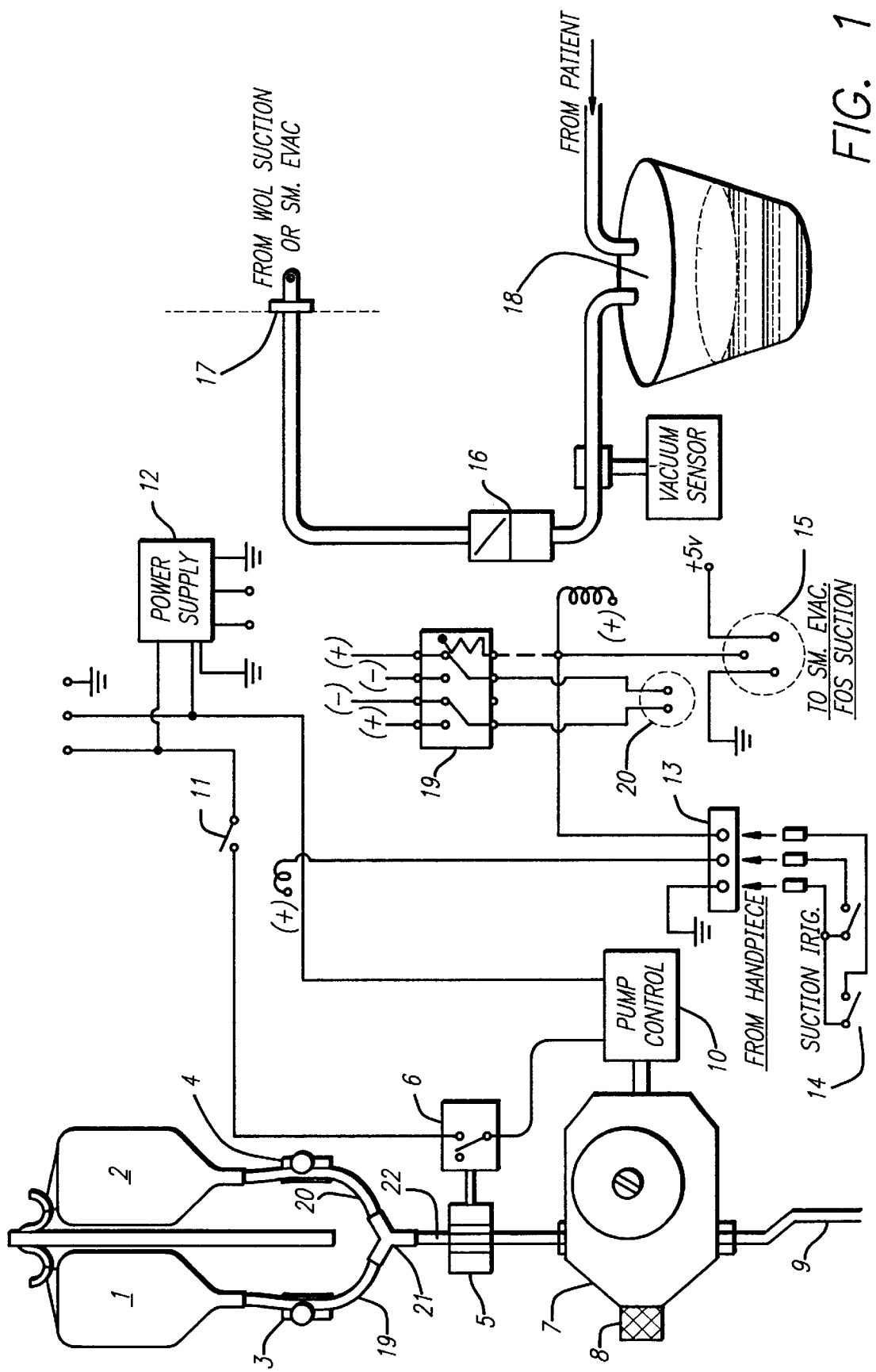
FIG. 1 is a simplified schematic block diagram of the fluid control system of the present invention.
Figures 1, 2:
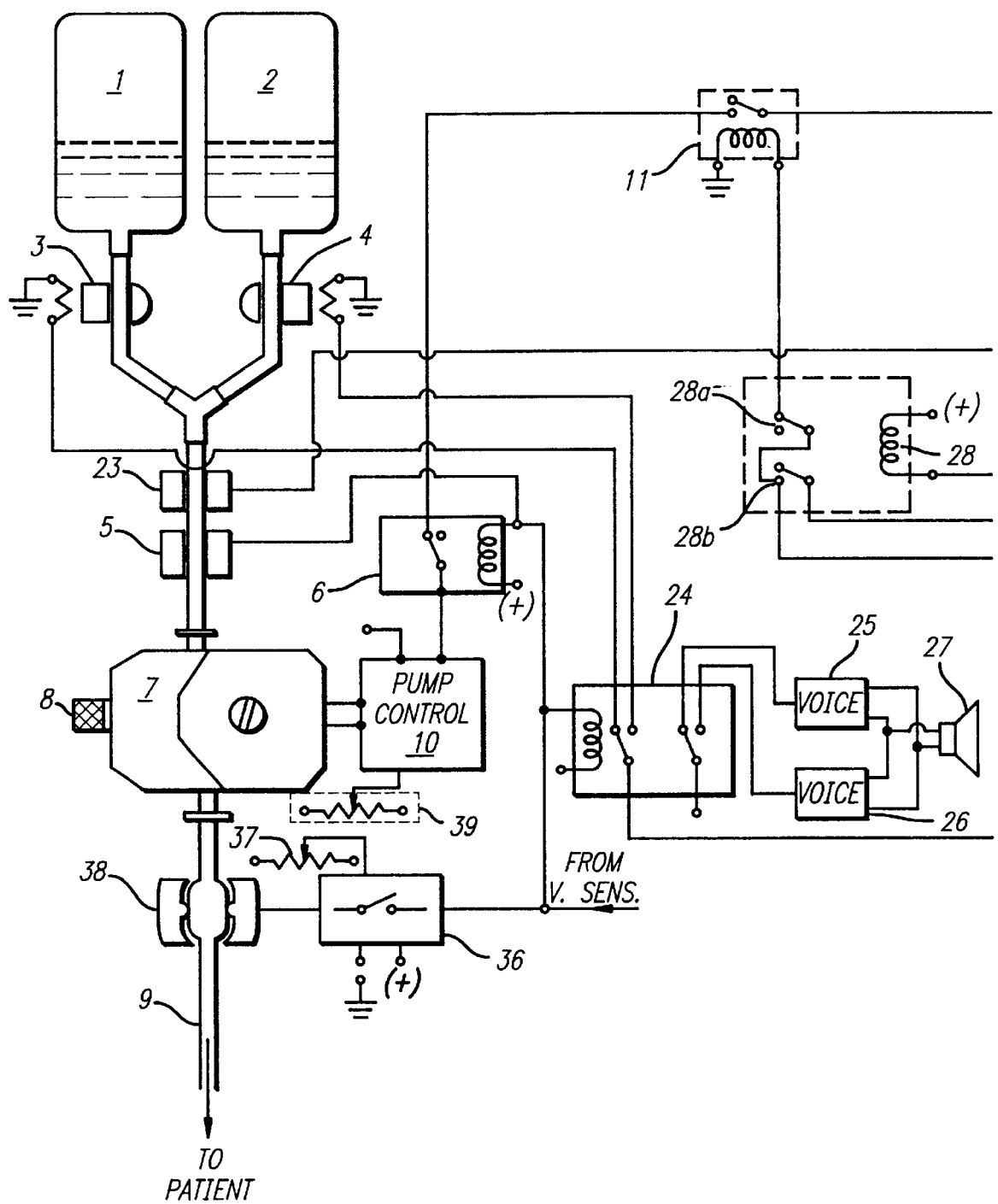
FIG. 2 is a complete schematic block diagram of the automatic fluid control system of the present invention.
Figure 2:
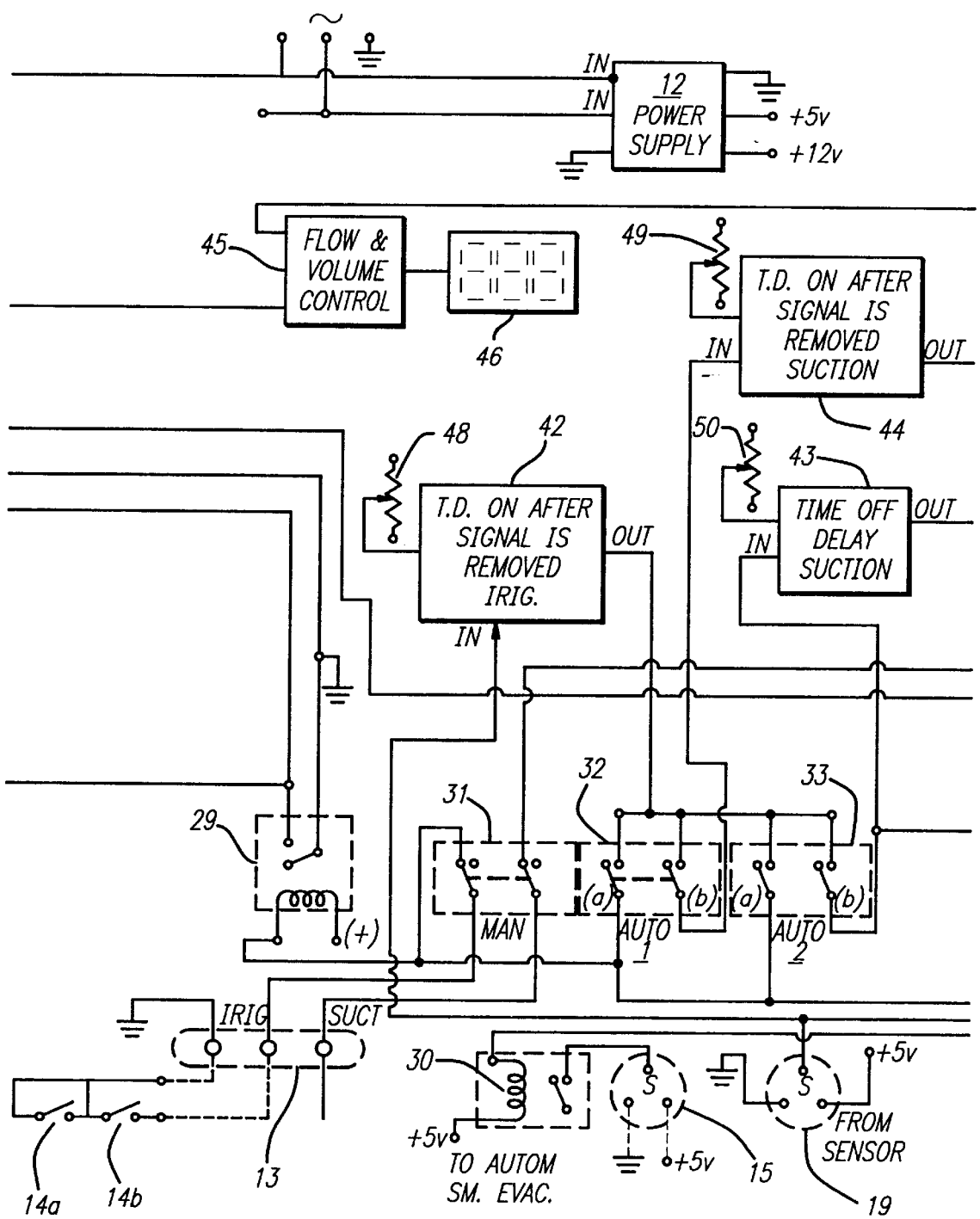

Block diagram schematics of the fluid control apparatus and system of the present invention are shown in FIGS. 1 and 2, with a simplified version of the apparatus and system shown in FIG. 1 and a more complete and thorough version of the system and apparatus shown in FIG. 2.

In FIG. 1, irrigation fluid containers 1 and 2 are set above the rest of the unit to provide a gravity water drop through tubings 19 and 20. This gravity water drop facilitates priming of the pump by eliminating the need to force the pump to work in order to draw water from a level below the height of the pump. The gravity water drop also increases water pressure and flow since the weight of the water will add pressure to the pressure generated by the pump. Although two separate containers 1 and 2 are shown in FIG. 1, the fluid control system of the present invention may employ one or several containers.

Tubes 19 and 20 are connected to containers 1 and 2, respectively, and the fluid flow through tubes 19 and 20 is controlled by valves 3 and 4, respectively. The fluid control apparatus may function with valves 3 and 4 in the open position either individually, or simultaneously. The ends of tubes 19 and 20, which are opposite their ends that are connected to containers 1 and 2, are attached to a Y connector 21 which is connected to a single tube 22 which passes through a sensor 5. The sensor 5 will detect when water is present in the tube 22. If water does not fill that portion of the tube 22 that is screened by the sensor 5, the sensor will open contact 6 thereby stopping the pump so that no air is pumped into the system.

From sensor 5, the water passes through pump 7 whose speed is controlled by pump controller 10. The pressure is controlled by controller 8 which will adjust and control the occlusion pressure of the pump 7.

The pump is activated by the switches located on the hand piece, later described with reference to FIG. 3, which is, represented in FIG. 1 by switches 14. The hand piece containing switches 14 is plugged into connector 13. When the irrigation switch 14 is pressed, relay 11 will close and the pump will start the irrigation thereby delivering water through tube 9 to the patient. This process happens while suction switch 14 is closed.

If an independent wall suction 17 or similar evacuation means is connected to this system, then the solenoid 16 will open and suction will be applied to suction canister 18. As a result of applying suction to suction canister 18, suction will be produced at the hand piece adaptor (also termed suction/irrigation connector) at port 72 shown in FIG. 4. Similarly, the irrigation fluid enters port 70 of the suction/irrigation connector shown in FIG. 4A.

If no wall suction or other independent suction device is available, the smoke evacuator system and apparatus detailed in U.S. patent application Ser. No. 5,199,944 may be connected to connector 15 shown in FIG. 1. When the suction switch on the automatic smoke evacuator system is activated, the smoke evacuator will turn on and will produce the suction necessary for providing the suctioning means function of the fluid control system of the present invention.

FIG. 2 represents a more complex schematic of the automatic fluid control system of the present invention. The basic principle of the fluid control system described with reference to FIG. 1 is the same as that shown in FIG. 2 with the exception that the automatic fluid control system described with reference to FIG. 2 includes additional capabilities and safety features beyond those contained in the basic unit.

Turning now to FIG. 2, multiple fluid containers 1 and 2 are shown which will have a fluid warmer (not shown) for maintaining their pre-warmed fluid temperature. In FIG. 2, manual valves 3 and 4 from FIG. 1 are replaced by automatic electronic valves which will open automatically when the irrigation is activated. One of the valves will remain closed until the fluid is used from the first container. At this time, sensor 5 will activate controller 6 and controller 24. Controller 6 will not allow the pump to operate until the fluid is present in the tube. As a result, controller 24 will switch automatically to the other container and will activate the alarm or "the voice" 25 or 26 which will announce through speaker 27 that the fluid container currently being used is empty and needs to be replaced. Controller 24 opens the valve to the full container and closes the valve to the empty container. As a result, fluid enters the tube and is detected at sensor 5 thereby allowing the pump to be activated if irrigation is needed.

The fluid control apparatus described in FIG. 2 will work in the manual mode as well as in an automatic mode. The system will have one or more automatic modes in addition to a Cysto Turp Mode.

In manual mode, activation of the irrigation function of this system is triggered by closing switch 14B. Switch 14B can be a switch of an electro surgery unit pencil or any hand piece or foot switch that is designated to control the suction and irrigation functions. When switch 31 is in the closed position as shown, relay 29 is activated. Manual switch 31, auto 1 switch 32, auto 2 switch 33, auto 3 switch 34, and Cysto Turp switch 35 are connected together and work in conjunction with one another such that when one of the switches is closed, all of the others remain open. After passing through relay 29, relay 28 is activated. The current passes through relay 28 with contacts 28B open and contacts 28A closed (in a normal, non-activated position). After passing through relay 28 at contacts 28A, the, current activates relay 11 which energizes pump controller 10. Pump controller 10 is activated if all of the above conditions are met and contact at controller 6 is closed.

Meanwhile, at the same time relay 29 is activated through controller 24, either valve 3 or 4 will open and allow the irrigation fluid to be delivered. This design can be modified to allow either valve 3 or 4 to stay continuously open until the irrigation fluid from its respective container is completely used up. Controller 24 will then switch to the other valve and open it to allow the irrigation fluid to flow through the tubing and be delivered to the patient.

The suction function of the fluid control system and apparatus is activated when switch 14A is closed. Again, considering manual switch 31 is closed and conditions are met, solenoid 16 is opened and allows for suction to be applied to suction canister 18. Suction canister 18 is connected to the patient via tubing which is connected to the hand piece of the electro surgery unit pencil that is being used for operation on the patient. When solenoid 16 is opened, a vacuum will be created in suction canister 18 thereby drawing fluid away from the patient and into the suction canister 18. The flow can be adjusted with flow adjust 51.

If a wall unit suction or other independent suctioning means is not available for use with the fluid control apparatus, the automatic smoke evacuator system previously described in U.S. patent application Ser. No. 5,199,944 may be used for providing a suctioning means. If the automatic smoke evacuator system is used for suction, it is connected to connector 15. Switch 47 will then be in the automatic smoke evacuator system position and when suction is activated, relay 30 is energized and the automatic smoke evacuator system will be activated in order to perform the suction.

Turning now to automatic mode 1, when auto 1 switch 32 is depressed, the manual switch 31 will open and sensor connector 19 will be included in the circuit. The electro surgery unit radio frequency sensor, which is described in U.S. patent application Ser. No. 5,318,516, which is herein incorporated by reference, can be placed in connector 19. A laser sensor, which is a light sensor with sensitivity to infrared, or a sensor for fiber optics used with lasers such as YAG, KTP, etc., which is clamped over a portion of the fiber and isolated from the external light is installed on the foot switch. When the laser is activated, the sensor will activate the automatic smoke evacuator system or fluid control system. Any of these sensors may be connected and used with the system of the present invention, thereby enabling a signal to be received by connector 19 when one of the surgical apparata are activated.

The first time delay solid state relay 42 is energized but not activated because this time delay solid state relay will activate only when the surgical device is deactivated and the signal is turned off. The signal from the first time delay relay 42 will travel to the two contacts 32a and 32b at the auto 1 switch 32. The signal will proceed from contact 32a to relay 29 which will then become activated and ultimately activate the irrigation pump just like the procedure previously outlined in reference with the manual mode. The time duration for the first time delay is adjusted by adjusting potentiometer 48.

The signal through contact 32b at auto 1 switch 32 will be delivered to a second time delay solid state relay 44, which is the same as the first time delay solid state relay 42, and will be energized but not activated until the signal is removed. The signal will be removed when the surgical device (laser or ESU) is deactivated. At this time, irrigation will be activated and remain on until the time period designated by adjusting potentiometer 48 has passed, the end of which time period will also be when the irrigation will stop. At this time, the third time delay solid state relay 44 will be activated thereby activating the suction just as previously described with reference to the manual mode. As a result, in automatic mode 1, the irrigation will turn on when the electro surgical device or laser is deactivated and the suction will turn on when the irrigation stops. The suction will start at the time that the suction is triggered "ON" after irrigation is off and will be on for a period of time determined by adjustment by adjusting potentiometer 49.

In automatic mode 2, auto 2 switch 33 is depressed and contacts 33A and 33B will be in the ON position and all other switches will be in the OFF position. The signal is outputted from sensor 19 and is delivered to the first time delay solid state relay at the IN gate. The output signal from the first time delay solid state relay 42 will travel from the OUT gate and through auto 2 switch 33. As the signal travels through contact 33A of auto 2 switch 33, irrigation is activated in the same way as previously described with reference to automatic mode 1. More specifically, the signal passing through contact 33A will proceed to solid state relay 29 which will activate the irrigation pump in the same way as described with reference to the previously described manual mode.

The output signal from the OUT gate of the first time delay solid state relay 42 will also pass through contact point 33B which will deliver the signal to the IN gate of the second time delay solid state relay 43 and activate the second time delay solid state relay 43. The second time delay solid state relay 43 will be activated at the same time that the irrigation is activated. However, when the irrigation is deactivated, the suction will run a few seconds longer than the irrigation. This time difference between irrigation shut off and suction shut off is adjusted by time adjust potentiometer 50.

Turning now to automatic mode 3, the signal from sensor connector 19 will reach auto 3 switch 34 which will be depressed in the ON position while all other switches remain in the OFF position. The signal outputted from sensor connector 19 passes through connection point 34A of the auto 3 switch 34 and is received from the IN gate of second time delay solid state relay 43. The output signal is outputted from the OUT gate of second time delay solid state relay 43 and will be activated at the same time that surgical devices, such as the electro surgery unit and laser, are activated. This output signal for suction will run for the same time period that the surgical device is employed plus an extra time period which is adjusted by adjusting potentiometer 50. The signal outputted from the OUT gate of third time delay solid state relay 43 will activate the suction means at the same time that the irrigation means is activated through connection point 34B of the auto 3 switch 34. The signal passes through connector point 34B to relay 29 thereby activating the irrigation means in the same way as previously described with reference to the manual mode. Due to the additional safety features of the automatic fluid control apparatus, automatic mode 3 can be used for surgery under water or for Cysto Turp thereby making it much safer for the patient.

The fluid control system and apparatus of the present invention is especially useful for under water surgery in that the water level is maintained by continuously replacing the suction water with fresh irrigation water thereby greatly enhancing visibility for the operator. The irrigation flow and volume are continually monitored by flow meter sensor 23 and suction flow meter sensor 22. Signals from flow meter sensor 23 and suction flow meter sensor 22 are received by counter 45 and the difference in fluid flow rates and fluid volume pumped in and taken out of the patient is reported and displayed on light emitter diode (LED) 46.

The safety of the automatic fluid control apparatus and method of the present invention is further improved by the inclusion of pressure sensor 38 which senses the fluid pressure of the irrigation fluid prior to delivery to the patient. The irrigation fluid pressure is read by the pressure sensor 38. Pressure controller 36 will activate relay 6 in the event that the pressure exceeds the safety limits which are set by adjusting potentiometer 37. When pressure controller 36 activates relay 6, the irrigation pump is turned off thereby avoiding delivery of the irrigation fluid at an unsafe pressure.

The suction function of the fluid control system and apparatus of the present invention is monitored by vacuum sensor 40. When a signal is emitted from vacuum sensor 40 it is transmitted to relay 41 which in turn will turn off the suction by opening contact point 41B of relay 41, and turn off irrigation by closing contact 41A of relay 41. Closing contact 41A of relay 41 will in turn activate relay 6 (the pump safety relay) thereby stopping the pump. This vacuum sensor feature will eliminate pressure build-up relating to the irrigation function of the fluid control system and apparatus thereby enabling automatic mode 3 to be safely used for Cysto Turp. The automatic mode 3 and/or manual mode can also be used for wound care with paper hand piece attachments.

The final mode for the automatic fluid control, system and apparatus of the present invention is CYSTO TURP mode. Cysto Turp Mode is activated by Cysto Turp switch 35 having contact points 35A and 35B. When Cysto Turp switch 35 is activated in the ON position, all other switches are in the OFF position.

When sensor 19 is activated, the signal emitted from sensor 19 is transmitted through Cysto Turp switch 35 which is closed. Contact point 35A of Cysto Turp switch 35 enables the signal to pass directly to a point of activation for suction. Meanwhile, the signal also passes through contact point 35B of Cysto Turp switch 35 and proceeds to activate relay 28 which in turn disconnects relay 11 and the irrigation pump. However, after passing through relay 28, the signal is transmitted to, and activates, relay 24 which will open either solenoid valve 3 or 4 thereby allowing the fluid to bypass the pump and undergo a gravitational flow. In this case, the irrigation fluid will be sucked by the suction which will help the flow of the irrigation fluid that would otherwise be determined by gravity only. This type of suction/irrigation flow will be very safe for Cysto Turp procedures where fluid pressure is of the utmost importance in carrying out a successful procedure.

Finally, with reference to FIG. 2 there is shown a connector 20 that will be used for connecting an automatic electrode retractor for suction/irrigation with an electro surgery unit electrode attachment. Relay 21 will automatically retract the electrode when suction is activated with the suction/irrigation device so that the electrode will not be in the way of the suction tip. This retraction of the electrode is reversed, and will further lock the exposed electrode in place, when electro surgery is employed. This automatic retraction and reversal was performed manually in the prior art.

Figures 2, 3:
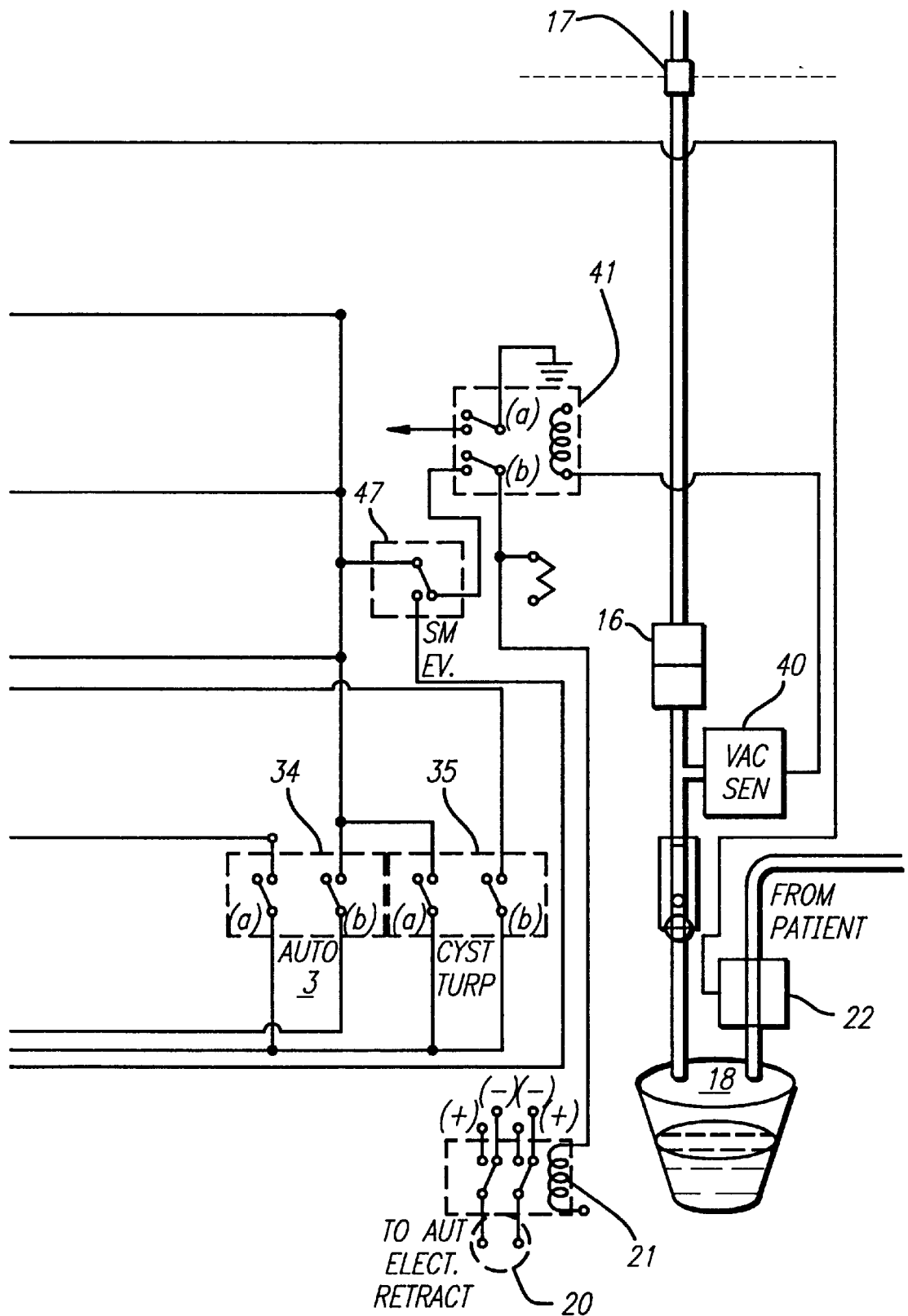
FIG. 3 shows a perspective view of a hand piece which is the subject of my previous patent application entitled "A Telescopic Surgical Device and Method Therefor", Ser. No. 08/500,045, which can be modified by the installation of additional apparatus shown in FIGS. 4 and 5, and then combined with the fluid control apparatus of the present invention, to provide a complete and efficient fluid control system.
Figure 3:
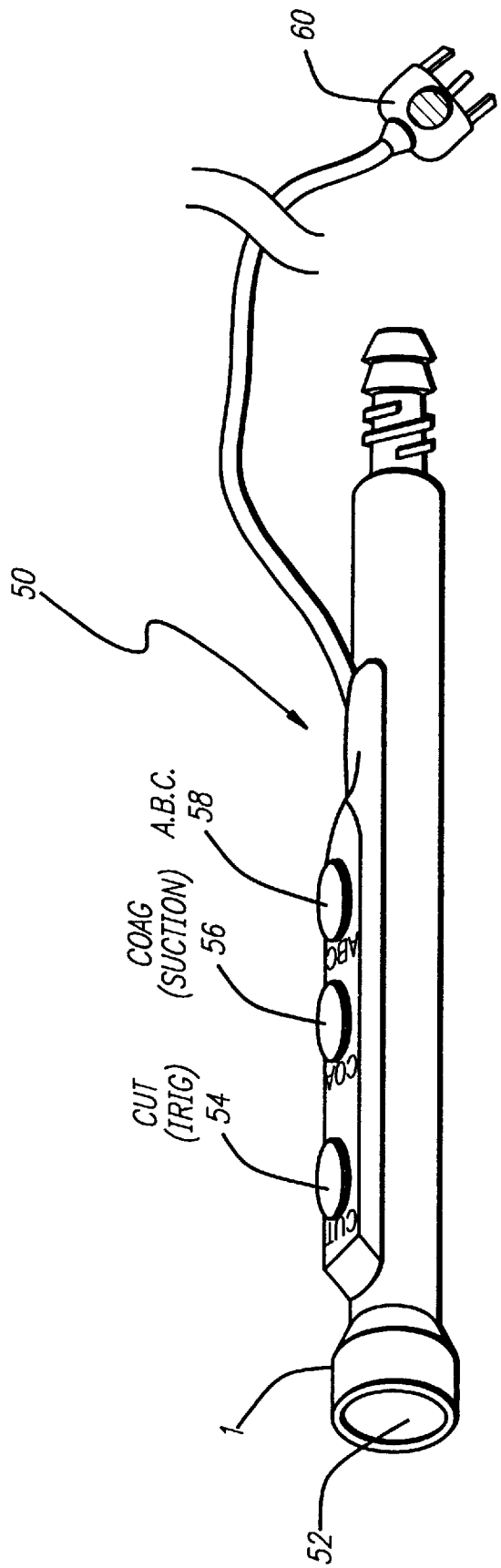

Turning now to FIG. 3, there is shown a hand piece 50 which is described in patent application Ser. No. 08/500,045 entitled "A Telescopic Surgical Device and Method Therefor". A new application for hand piece 50 is created by removing the telescopic portion (not shown) of hand piece 50 thereby revealing a threaded receiver 52 at its anterior end which can be used for receiving attachments later described in reference to FIGS. 4 and 5. In its previously described application, hand piece 50 comprised an activation switch for cutting, an activation switch for coagulation, and an activation switch for argon beam coagulation. However, when used with the fluid control system and apparatus in its new application, the cutting activation switch 54 of the hand piece is now used to activate suction while the coagulation activation switch 56 is now used to activate irrigation. Connector 60 of hand piece 50 is plugged into connector 13 of the fluid control apparatus shown in FIGS. 1 and 2.

FIG. 4A illustrates suction/irrigation connector (adaptor) 62 which is specially designed for application with the fluid control system and apparatus of the present invention, and will replace the trumpet valve used with other suction/irrigation systems and apparata previously described in reference to the prior art. The suction/irrigation connector (adaptor) 62 can be used with an external tube, such as those shown in FIGS. 4B and 4C, connected at its anterior end, or alternatively, the suction/irrigation connector (adaptor) 62 may be connected at its posterior end to hand piece 50 shown in FIG. 3. Port 70 functions as the irrigation connector which will be connected to tubing 9 extending from the irrigation pump and fluid containers as shown in FIGS. 1 and 2. On the other hand, port 72 functions as the suction connector which is connected to suction tubing coming from the suction canister 18 shown in FIGS. 1 and 2.

The suction/irrigation connector (adaptor) 62 comprises a female threaded portion 74 located at its posterior end for connecting hand piece 50, shown in FIG. 3, to the suction/irrigation connector (adaptor) 62. Threaded male connector portion 76 is located at the anterior end of the suction/irrigation connector(adaptor) 62 for connection to an external tube such as those shown in FIGS. 4B and 4C. The suction/irrigation connector (adaptor) 62 further includes a first widened channel 78 which is continuous with a second narrow channel 80, with the second narrow channel 80 ending in exit port 82. The suction/irrigation connector (adaptor) 62 also comprises a protuberance 84 which functions to retain a cap element 85, a cross section of which is shown in FIG. 4D, over exit port 82 and female threaded portion 74 in order to guard against fluid leaks while the fluid is under pressure.

FIG. 4B shows a suction/irrigation tube 86 which functions to enable suction and irrigation to occur simultaneously. The suction/irrigation tube 86 comprises a first hollow tube 88 contained within a second, larger hollow tube 90, wherein the posterior end 92 of the first hollow tube 88 extends beyond the posterior end of the second, larger hollow tube 90. The second, larger hollow tube 90 further comprises a female connector 94 located at its posterior end and a plurality of circumferentially positioned openings 96 positioned about its tapered anterior end.

In use, female connector 94 of suction/irrigation tube 86 is connected to male threaded portion 76 of suction/irrigation connector (adaptor) 62. Posterior end 92 of first hollow tube 88 is seated within widened channel 78 and narrow channel 80 such that the irrigation channel is separated from the suction channel. First hollow tube 88 is contained within the hollow anterior of the second larger, hollow tube 90. The ring-like channel created by the configuration of first hollow tube 88 and second larger, hollow tube 90 functions to contain and direct the suction which is performed with the fluid control system and apparatus of the present invention. The multiple circumferentially positioned openings 96 located at the anterior end of suction/irrigation tube 86 function to allow the suction to access the fluid. Meanwhile, irrigation fluid travels through the center of first hollow tube 88 and is emitted from opening 98 located at the anterior end of suction/irrigation tube 86. This unique configuration of the suction/irrigation connector (adaptor) 62 and suction/irrigation tube 86 enable suction and irrigation to be performed either separately or simultaneously.

Another embodiment of suction/irrigation tube 86 shown in FIG. 4B is illustrated in FIG. 4C. More specifically, suction/irrigation tube 100 comprises a posterior end having a male connector 102 and an anterior end having a plurality of circumferentially positioned openings 104. Female connector 102 is connected to threaded male portion 76 of suction/irrigation connector (adaptor) 62. However, with suction/irrigation tube 100, suction and irrigation cannot be performed simultaneously, and must be employed separately.

FIG. 4E illustrates a top elevational view of the specially designed hand piece for use in conjunction with the fluid control system and apparatus of the present invention. The specially designed hand piece comprises a suction/irrigation tube 86, which may be telescopic, which is connected to suction/irrigation connector (adaptor) 62, which is connected to hand piece 50 which was previously described with reference to FIG. 3.

A cross sectional view of an electro surgical connector 110 is shown in FIG. 5. Electro surgical connector 110 comprises a first housing member 112, a second housing member 114, which is seated within the posterior end of first housing member 112, and a third housing member 116 which is connected at its anterior end to the posterior end of second housing member 114. Third housing member 116 comprises an anterior end 118, a posterior end 120, a conductive channel 122 running from its anterior end 118 to its posterior end 120, and a connector 124 which will be connected through an electrical cord to an electro surgical generator for activation using a foot switch. Third housing member 116 also comprises threaded female connector portion 126 and contacts 128 located at its posterior end 120.

Electrode 130 comprises an anterior end 132 and a posterior end 134, and is seated within second housing member 114. Anterior end 134 of electrode 130 is located near second housing element 114 such that anterior end 34 of electrode 130 extends beyond second housing element 114. Electrode 130 is connected to third housing element 116 by inserting posterior end 134 of electrode 130 into third housing member 116. Meanwhile, anterior end 136 of second housing member 114 is located within widened channel 138 contained within first housing member 112. Anterior end 132 of electrode 130 extends out beyond anterior end 140 of first housing member 112.

The configuration of second housing member 114 containing electrode 130 and first housing member 112 allows for the retraction of electrode 130 when suction and/or irrigation is desired during electro surgery. An "O" ring is installed at anterior end 136 of second housing member 114 to prevent gas from escaping during laparoscopy. "O" ring 142 also prevents second housing member 114 and first housing member 112 from separating during the procedure in that "O" ring 142 will lodge against abutment 144 to prevent the separation of first housing member 112 from second housing member 114 at the point of greatest retraction. The retraction of electrode 130 is reversed when the operator recommences with electro surgery.

If the electro surgical connector 110 is used with hand piece 50, described in FIG. 3, contacts 128 are connected to contacts located within the inside of hand piece 50 to establish electrical contact. Electrode 130 may comprise varying shapes including, but not limited to, a blade shape, a needle shape, and a hook shape. First housing member 112 comprises a threaded male connector 146 at its anterior end which can be connected to female threaded portion 74 of suction/irrigation connector (adaptor) 62. If suction/irrigation connector (adaptor) 62 is used, electrode 130 is introduced into posterior end 92 of first hollow tube 88 (shown in FIG. 4B) and exits first hollow tube 88 at opening 98 located at its anterior end (shown in FIG. 4B). Electrode 130 may also be used with, and introduced into, suction/irrigation tube 100 (see FIG. 4C).

Figure 5A:
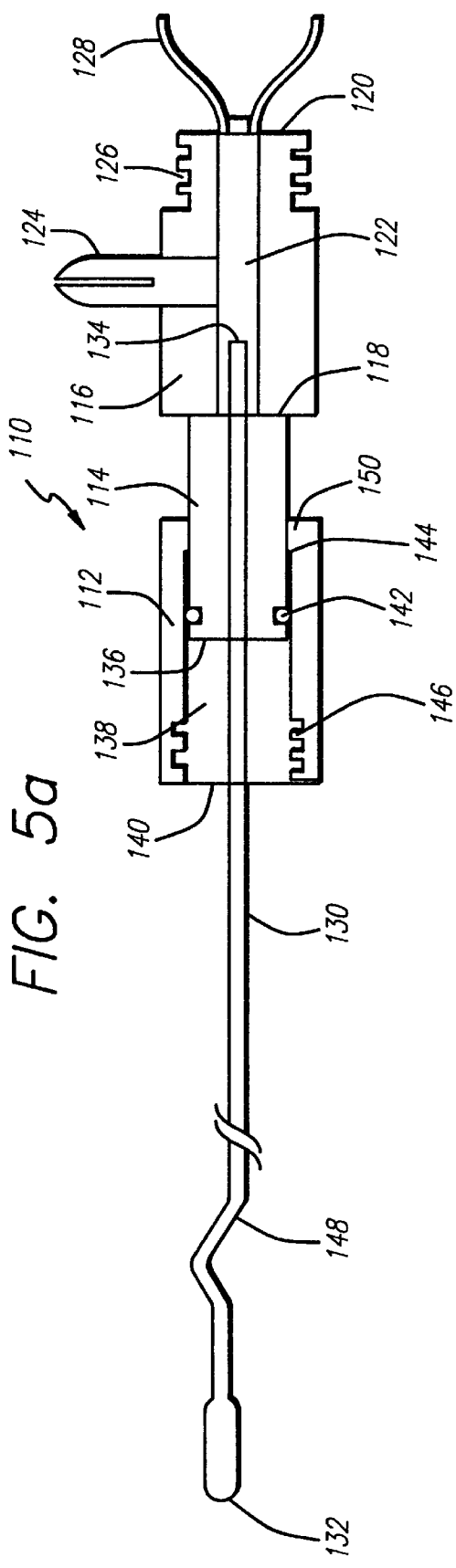
FIG. 5A is a cross-sectional view of the electrosurgical connector of the present invention which is connected to the suction/irrigation connector at its anterior end, and to the hand piece having on and off switches at its posterior end, with an electrode inserted through channels contained within the electro surgical connector.

Electrode 130 shown in FIG. 5A comprises an S shape bend 148 thereby allowing it to be fixed and centered inside suction/irrigation tube 86 or suction/irrigation tube 100. In order to expose anterior end 132 of electrode 130 from suction/irrigation tube 86 or 100, first housing member 116 is pushed forward toward posterior end 150 of first housing member 112. Conversely, when third housing member 116 is pulled away from posterior end 150 of first housing member 112, anterior end 132 or electrode 130 will be retracted within suction/irrigation tubing 86 or 100 so that suction and/or irrigation can be performed without obstruction by anterior end 132 of electrode 130.

Figure 5B:
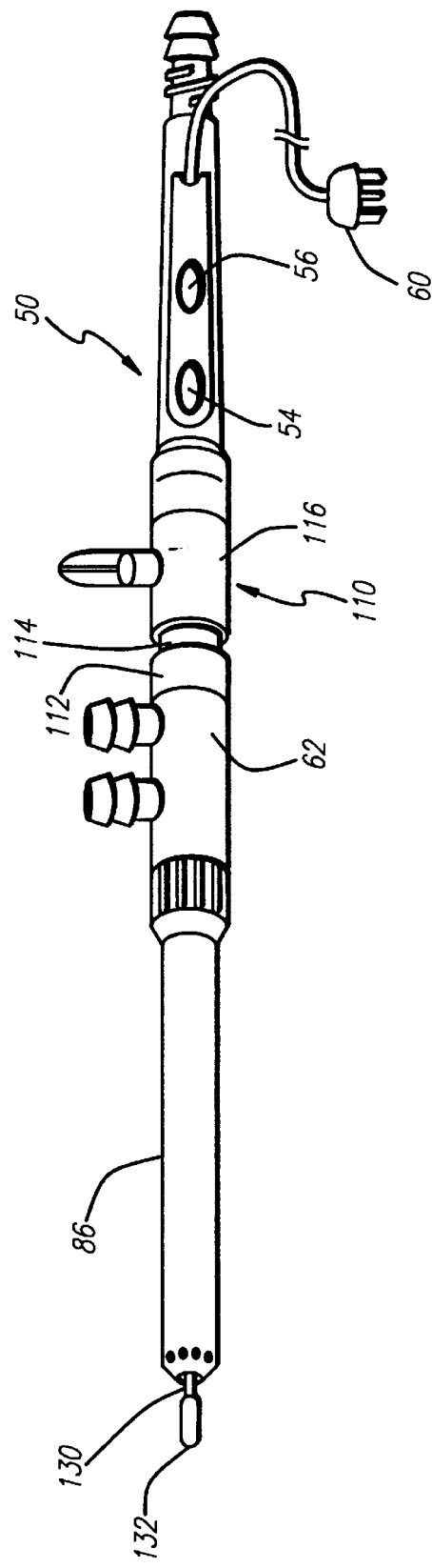
FIG. 5B is a top elevational view of an electrosurgery wand comprising an electrode, the suction/irrigation tube, the suction/irrigation connector, the electro surgical connector, and the hand piece having on and off switches, all being connected in that order.

FIG. 5B illustrates a top elevational view of a completely constructed hand piece specifically designed for use with the fluid control system and apparatus of the present invention. Suction/irrigation tube 86 is connected to suction/irrigation connector (adaptor) 62, which is connected to electro surgical connector 110, which is in turn connected to hand piece 50, all being connected in that order. Electrode 130 is inserted through channels contained in suction/irrigation tube 86, suction/irrigation connector (adaptor) 62 and electro surgical connector 110, with the anterior end 132 of electrode 130 extending beyond opening 98 in suction/irrigation tube 86. As previously described, connector 60 is connected to connector 20 (shown in FIG. 2) thereby enabling the specially designed hand piece unit illustrated in FIG. 5B to work in conjunction with the fluid control system and apparatus of the present invention shown in FIG. 2.

While preferred embodiments of the invention have been shown and described, it will be apparent to those skilled in this art that various modifications may be made on these embodiments without departing from the spirit of the present invention.

I claim:

1. A multifunctional handpiece for performing suction and irrigation comprising:

an elongated hollow member comprising an outer annular channel and an inner central channel disposed axially within said outer annular channel; and a suction/irrigation adaptor connected to said elongated hollow member, said suction/irrigation adaptor having a suction port and an irrigation port wherein said outer annular channel of said elongated hollow member is in fluid communication with said suction port and said inner central channel of said elongated hollow member is in fluid communication with said irrigation port.

2. The multifunctional handpiece of claim 1, further comprising:

a handpiece member connected to said suction/irrigation adaptor, said handpiece member having electrical contacts for activating a suction device and an irrigation device.

3. The multifunctional handpiece of claim 1, further comprising an electrosurgical connector connected to said suction/irrigation adaptor, said electrosurgical connector comprising an electrode which extends from said electrosurgical connector through said suction/irrigation adaptor and said elongated hollow member and extends beyond said elongated hollow member, said electrode being in electrical communication with an electrosurgical generator.

4. The multifunctional handpiece of claim 3, said electrosurgical connector further comprising a first member fixedly attached to said electrode and a second member disposed annularly around said first member, said first member being slidably received within said second member such that said first member may be moved from a first position relative to said second member to a second position relative to said second member, wherein said electrode can be retracted into said elongated hollow member by moving said first member from said first position to said second position.

5. A multifunctional handpiece for performing suction and irrigation in conjunction with electrosurgery and laparoscopy comprising:

a suction/irrigation adaptor having a suction port and an irrigation port;

an elongated hollow member comprising an outer annular channel and an inner central channel disposed within said outer annular channel, said outer annular channel being in fluid communication with said suction port and said inner central channel being in fluid communication with said irrigation port; and a handpiece member connected to said suction/irrigation adaptor, said handpiece member having electrical contacts for activating a suction device and an irrigation device.

6. The multifunctional handpiece of claim 5, further comprising an electrosurgical connector connected to said suction/irrigation adaptor, said electrosurgical connector comprising an electrode which extends from said electrosurgical connector through said suction/irrigation adaptor and said inner central channel of said elongated hollow member, and extending beyond said elongated hollow member.

* * * * *